United States Patent [19]

Lin et al.

[11] Patent Number: 4,600,575
[45] Date of Patent: Jul. 15, 1986

[54] AEROSOL ANESTHETIC COMPOSITIONS

[75] Inventors: Song-Ling Lin; Moo-Kwang Park, both of Rouses Point, N.Y.

[73] Assignee: American Home Products Corporation, New York, N.Y.

[21] Appl. No.: 263,531

[22] Filed: May 14, 1981

Related U.S. Application Data

[63] Continuation-in-part of Ser. No. 18,535, Mar. 8, 1979, abandoned.

[51] Int. Cl.$^4$ .................. A61K 31/24; A61L 9/04
[52] U.S. Cl. ........................ 424/45; 514/535; 514/536; 514/817; 514/971
[58] Field of Search ............... 424/45, 173, 310; 514/535, 536, 817, 971

[56] References Cited

U.S. PATENT DOCUMENTS

| | | | |
|---|---|---|---|
| 2,187,597 | 1/1940 | Blaso | 424/45 |
| 2,382,546 | 8/1945 | Curtis | 424/185 |
| 2,457,188 | 12/1948 | Stone | 424/310 |
| 2,628,182 | 2/1953 | Reasenberg | 424/310 |
| 3,322,624 | 5/1967 | Stone | 424/45 |
| 3,808,319 | 4/1974 | Kanfoush | 424/308 |
| 4,052,513 | 10/1977 | Kaplan | 424/310 |
| 4,174,295 | 11/1979 | Bargigia | 424/45 |

OTHER PUBLICATIONS

American Perfumer and Cosmetics; Oct. 1962, p. 128.
McCutcheon's Det. & Emul., 1971 Annual, p. 195.

*Primary Examiner*—Allen J. Robinson
*Attorney, Agent, or Firm*—Adley F. Mandel

[57] ABSTRACT

Novel liquid anesthetic aerosol composition comprising high concentrations of benzocaine in a water washable base with propellants which are resistant to cold temperatures are disclosed.

5 Claims, No Drawings

AEROSOL ANESTHETIC COMPOSITIONS

This is a continuation in part application of application Ser. No. 18,535, filed Mar. 8, 1979, now abandoned.

BACKGROUND OF THE INVENTION

1. Field of the Invention

This invention relates to liquid compositions of anesthetic agents in aerosol containers. More specifically, this invention relates to liquid compositions of the anesthetic benzocaine which form single phase mixtures in combination with solvent and hydrocarbon propellants, and which remain single phase at low temperatures and high concentrations of benzocaine.

2. Description of Related Art

Benzocaine, the ethyl ester, ester of p-aminobenzoic acid, is a well known local anesthetic which has been topically administered in the form of ointments, lotions, sprays, gels and as an impregnant in first aid pads. In order to enhance or prolong benzocaine's anesthetic activity, various efforts have been made to increase the concentration of benzocaine in various solvents or to more effectively maintain the anesthetic at its site of administration. Increasing the concentration of benzocaine, however, had to be balanced against the increasing probability of benzocaine precipitation, particularly at colder temperatures, thereby limiting their field of use. The goal of formulating highly concentrated benzocaine compositions characterized by cold temperature resistance is even greater in aerosol anesthetic compositions wherein even small amounts of precipitate can clog valves or orifices, and wherein sufficient pressure must be maintained to both completely deliver all the benzocaine solution within the container and evenly distribute the benzocaine solution with desirable spray characteristics.

Many solvents have been disclosed for benzocaine. For example, U.S. Pat. No. 2,187,597 discloses anesthetic formulations containing up to five percent of the anesthetic agent in a mixture of benzyl alcohol and ethyl chloride. Other formulations containing up to 10% benzocaine in mixtures with a procaine salt, water, water miscible poly-hydroxy aliphathic alcohols and their ethers have been disclosed in U.S. Pat. No. 2,382,546. U.S. Pat. No. 2,457,188 discloses benzocaine solutions containing at least 10% benzocaine at 20° C. utilizing solvents selected from certain polyoxyalkylene glycols, aliphatic ethers of dihydric alcohols, aromatic ethers of aliphatic dihydric alcohols, carboxylic acid esters of aliphatic dihydric alcohols, and carboxylic acid esters of aromatic and aliphatic ethers of aliphatic dihydric alcohols. In U.S. Pat. No. 2,682,182, benzocaine solutions containing up to 16% benzocaine at 0° C. were disclosed in a mixture employing a major amount of propylene glycol and a polyoxyethylene (8-25) hexitan monolaurate.

Anesthetic aerosol preparations containing at least 10% benzocaine in diesters of $C_8$-$C_{12}$ carboxylic acids and polyethylene glycols having a molecular weight of appoximately 300-600, and a propellant system made from mixture of chlorofluorohydrocarbons have been disclosed in U.S. Pat. No. 3,322,634. These aerosol formulations, however, are no longer acceptable because of certain atmospheric effects associated with chlorofluorohydrocarbons.

Benzocaine has also been employed in formulations containing certain other therapeutic ingredients, for example, as disclosed in U.S. Pat. No. 3,808,319 wherein the solvent is volatile alcohol such as ethyl alcohol or isopropyl alcohol. Solvents of this type, however, are generally counterproductive to desirable anesthetic properties because of their stinging nature to sensitive or wounded skin and the like. Compositions containing up to 15% benzocaine are further disclosed in U.S. Pat. No. 4,052,513 in the form of oil in water emulsions.

SUMMARY OF THE INVENTION

This invention provides liquid anesthetic compositions in aerosol containers. The composition of this invention comprises a single phase mixture of a water washable base of the preferred anesthetic benzocaine in a solvent and a propellant.

The weight percent of the benzocaine in the solvent is from about 0.5% up to its maximum solubility in the solvent. Selection of the solvent is made from the group consisting of polyoxyethylene sorbitan trioleate having an average of about 20 units of ethylene oxide in the molecule polyethylene glycol monolaurate wherein the polyethylene glycol has an average molecular weight of about 200 to about 600 and mixtures thereof. The propellant of the compositions of this invention comprises a mixture of difluoroethane and a hydrocarbon selected from the group consisting of n-butane, iso-butane and n-propane.

This invention is further defined by the provision that the composition is a single phase mixture after exposure to temperatures of about −20° C. when the benzocaine comprises about 20% by weight of the water washable base of benzocaine and solvent.

While the invention is illustrated with the anesthetic benzocaine, it will be apparent to those skilled in the art that the composisition of this invention is also suitable for other therapeutic agents deliverable from aerosol containers in which water washability, single phase cold temperature resistance and nonstinging of solvents are desirable characteristics.

DETAILED DESCRIPTION OF THE INVENTION

This invention relates to liquid anesthetic compositions in aerosol containers comprising a single phase mixture of a water washable base of benzocaine in a solvent and a propellant. The weight percent of benzocaine in the water washable base is from about 0.5% up to its maximum solubility in the solvent. For most effective anesthetic properties, the benzocaine comprises at least 10% by weight of the base and preferred compositions contain about 20% by weight of benzocaine.

Solvents useful in this invention are selected from the group consisting of polyoxyethylene sorbitan trioleate having an average of about 20 units of ethylene oxide in the molecule polyethylene glycol monolaurate wherein the polyethylene glycol preferably has an average molecular weight of about 400, and mixtures thereof. Although wider ranges of one solvent to another are acceptable, the solvent is preferably a mixture of the herein listed solvents in a ratio of 40:60 to each other, and most desirably in a ratio of 50:50.

The propellant system comprises a mixture of difluoroethane and a hydrocarbon selected from the group consisting of n-butane, isobutane and n-propane. In the preferred system which utilized n-butane, the difluoroethane comprises about 35-70% by weight of the propellant system. In the most preferred embodiments each of the propellants in a two propellant system comprise about 50% of the total propellant.

Further, the water washable base of benzocaine in solvent and the propellant each comprises about 45% to about 55% by weight of the liquid anesthetic composition, and in preferred embodiments, about 50%.

The compositions of this invention are further defined by the provision that the compositions form a single phase, clear liquid solution following exposure to temperatures of −20° C, when the benzocaine comprises about 20% of said water washable base, and in preferred embodiments, the composition is a single phase mixture at about −20° C. Compositions having the most preferred single phase characteristics at −20° C. employ the polyethyleneglycol monolaurate, or mixtures of polyoxyethylene sorbitan trioleate with the polyethyleneglycol monolaurate as the solvent.

lar to ARC-KN-37 (Ethyl Products Co., North Riverside, Ill.).

The invention is further illustrated by the following examples:

The following bulk concentrates (water washable base of benzocaine in solvent) were prepared for further evaluation,

|  | BULK CONCENTRATES | |
|---|---|---|
|  | I | II |
| Benzocaine | 20% | 20% |
| Menthol | 0.5% | 0.5% |
| Methylparaben | 1.0% | 1.0% |
| Polyoxyethylene 20 Sorbitan Trioleate | 78.5% | — |
| PEG 400 Monolaurate | — | 78.5% |

| Example # | Bulk Concentrates | | Propellants | | Pressure | Physical Stability | |
|---|---|---|---|---|---|---|---|
|  | I | II | difluoroethane | n-butane | psig @ 70° F. | RT | −20° C. (for 1 day) |
| 1. | 25% | 25% | 25% | 25% | 57 | OK* | OK |
| 2. | 22.5% | 22.5% | 27.5% | 27.5% | 71** | OK | OK |
| 3. | 27.5% | 27.5% | 22.5% | 22.5% | 71** | OK | OK |
| 4. | — | 50% | 35% | 15% | — | OK | OK |
| 5. | — | 50% | 30% | 20% | 57 | OK | ppt. OK @ RT |
| 6. | — | 50% | 25% | 25% | 56 | OK | ppt. OK @ RT |
| 7. | — | 50% | 20% | 30% | 51 | OK | ppt. OK @ RT |
| 8. | 25% | 25% | 35% | 15% | 63 | OK | OK |
| 9. | 10% | 40% | 30% | 20% | 60 | OK | OK |
| 10. | 25% | 25% | 30% | 20% | 58 | OK | OK |
| 11. | 25% | 25% | 25% | 25% | 57 | OK | OK |
| 12. | 25% | 25% | 20% | 30% | 52 | OK | OK |
| 13. | 25% | 25% | 15% | 35% | — | Separation | — |
| 14. | 25% | 25% | 18% | 32% | — | OK | OK |
| 15. | 25% | 25% | 25% | 25% | 57 | OK | OK |
| 16. | 20% | 30% | 25% | 25% | 79** | OK | OK |
| 17. | 30% | 20% | 25% | 25% | 78** | OK | OK |

*One phase system, clear solution
**Measured at RT

In formulating the composition of this invention, other ingredients, such as antipruritic agents, anit-infectives, anti-fungal agents and anti-bacterial agents are typically incorporated.

The following composition is an illustration of a preferred embodiment of this invention:

| Water Washable Base | |
|---|---|
| Benzocaine | 200.0 g |
| Menthol | 5.0 g |
| Methylparaben | 10.0 g |
| Polyoxyethylene 20 Sorbitan Trioleate | 392.5 g |
| Polyethyleneglycol 400 Monolaurate | 392.5 g |

The composition of the invention may be prepared by charging the solvent into a suitable container equipped with a stirrer, adding the benzocaine and/or other active ingredients and mixing until dissolution. The solution is then filtered through a suitable screen and loaded into an aerosol container along with the propellants in a conventional manner.

A suitable container for the composition of this invention is a can having a "2P" rating as specified by the United States Department of Transportation. Among the valve systems which have been employed satisfactorily in any position are those similar to a Seaquist NS-36 or NS-34 (Seaquist Valve Co., Cary, Ill.) or those simi-

What is claimed is:

1. A liquid anesthetic composition in an aerosol container consisting essentially of a single phase mixture of a water washable base of benzocaine in a solvent and a propellant wherein, a. the weight percent of said benzocaine is from about 0.5% up to its maximum solubility in the solvent;

b. the solvent is selected from the group consisting of polyethylene glycol monolaurate and mixtures of about 40% to about 60% of said polyoxyethylene sorbitan trioleate having an average of 20 units of ethylene oxide in the molecule with about 40% to about 60% of said polyethylene glycol monolaurate wherein the polyethylene glycol has an average molecular weight of about 400;

c. the propellant comprises about 45% to about 55% by weight of the composition and consists essentially of a mixture of about 35% to about 70% by weight of difluoroethane and about 30% to about 65% by weight of a hydrocarbon selected from the group consisting of n-butane, isobutane, n-propane and mixtures thereof
with the proviso that the composition remains a single phase mixture after exposure to temperatures of about −20° C. when the benzocaine comprises about 20% of said base.

2. The composition of claim 1 wherein the benzocaine comprises at least 10% of the water washable base.

3. The composition of claim 1 which is a single phase mixture at about −20° C. when the benzocaine comprises about 20% of said base.

4. A liquid anesthetic composition in an aerosol container consisting essentially of a single phase mixture of a water washable base of benzocaine in a solvent and a propellant wherein said base comprises by weight about 10% to about 20% benzocaine, about 40% to about 60% polyoxyethylene sorbitan trioleate having an average of about 20 untis of ethylene oxide in the molecule and about 40% to about 60% polyethylene glycol monolaurate, said polyethylene glycol having an average molecular weight of about 400; said propellant comprises by weight about 35% to about 70% difluoroethane and about 30% to about 65% of a hydrocarbon selected from the group consisting of n-butane, isobutane and n-propane; and wherein each of said base and said propellant comprise about 45% to about 55% of the composition.

5. A liquid anesthetic composition in an aerosol container consisting essentially of a single phase mixture of a water washable base of benzocaine in a solvet and a propellant wherein said base consists essentially of by weight about 20% benzocaine, about 40% polyoxyethylene sorbitan trioleate having an average of about 20 units of ethylen oxide in the molecule and about 40% polyethylene glycol monolaurate, said polyethylene glycol having an average molecular weight of about 400; said propellant consists essentially of about a 50:50 by weight mixture of difluoroethane and n-butane; and wherein each of said base and propellant comprise about 50% of the composition.

* * * * *